United States Patent
Sugimoto

(10) Patent No.: US 9,416,075 B2
(45) Date of Patent: Aug. 16, 2016

(54) METHOD FOR PURIFYING 2-FLUOROBUTANE

(71) Applicant: ZEON CORPORATION, Tokyo (JP)

(72) Inventor: Tatsuya Sugimoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/904,486

(22) PCT Filed: Jul. 16, 2014

(86) PCT No.: PCT/JP2014/068886
§ 371 (c)(1),
(2) Date: Jan. 12, 2016

(87) PCT Pub. No.: WO2015/008781
PCT Pub. Date: Jan. 22, 2015

(65) Prior Publication Data
US 2016/0145177 A1    May 26, 2016

(30) Foreign Application Priority Data
Jul. 19, 2013  (JP) .................................. 2013-150885

(51) Int. Cl.
| | |
|---|---|
| *C07C 17/395* | (2006.01) |
| *C07C 17/383* | (2006.01) |
| *C07C 17/02* | (2006.01) |
| *C07C 17/013* | (2006.01) |

(52) U.S. Cl.
CPC .............. *C07C 17/395* (2013.01); *C07C 17/02* (2013.01); *C07C 17/383* (2013.01); *C07C 17/013* (2013.01)

(58) Field of Classification Search
CPC ...... C07C 17/395; C07C 17/02; C07C 17/013
See application file for complete search history.

(56) References Cited

U.S. PATENT DOCUMENTS

| | | | |
|---|---|---|---|
| 2,550,953 | A | 5/1951 | Barrick et al. |
| 2011/0068086 | A1 | 3/2011 | Suzuki et al. |

FOREIGN PATENT DOCUMENTS

| | | |
|---|---|---|
| JP | 59-46251 A | 3/1984 |
| JP | 2001-226318 A | 8/2001 |
| JP | 2009-292749 A | 12/2009 |
| JP | 2013-95669 A | 5/2013 |
| WO | 2009/123038 A1 | 10/2009 |

OTHER PUBLICATIONS

Winstein, S. et al. J. Am. Chem. Soc., 1939, 61 (6), pp. 1576-1581.*
Written Opinion of the International Searching Authority dated Sep. 22, 2014, issued in counterpart International PCT Application No. PCT/JP2014/068886, (5 pages).
International Search Report dated Sep. 22, 2014, issued in counterpart application No. PCT/JP2014/068886 (2 pages).
Erickosn, et al., "Bromohydrins of Methylenecyclobutane", Journal of Organic Chemistry, 1971, vol. 36, No. 19, pp. 2915-2916.

* cited by examiner

*Primary Examiner* — Fereydoun G Sajjadi
*Assistant Examiner* — Medhanit Bahta
(74) *Attorney, Agent, or Firm* — Westerman, Hattori, Daniels & Adrian, LLP

(57) ABSTRACT

The present invention is a method for 2-fluorobutane to obtain highly purified 2-fluorobutane through a process comprising a step for: bringing crude 2-fluorobutane that includes 5 to 50 wt % of butene into contact with a brominating agent that can form a bromonium ion in an aprotic polar solvent in the presence of water or an alcohol having up to 4 carbon atoms; converting the butene into compounds having a boiling point higher than that of 2-fluorobutane, then recovering 2-fluorobutane from the reaction solution; and purifying the recovered 2-fluorabutane by distillation.

5 Claims, No Drawings

METHOD FOR PURIFYING 2-FLUOROBUTANE

TECHNICAL FIELD

The present invention relates to 2-fluorobutane that is useful as a plasma reaction gas that is used when producing a semiconductor device, a fluorine-containing medicine intermediate, a hydrofluorocarbon-based solvent, and the like. High-purity 2-fluorobutane is particularly suitable as a plasma reaction gas (e.g., plasma etching gas and CVD gas) that is used when producing a semiconductor device utilizing a plasma reaction.

BACKGROUND ART

Semiconductor production technology that achieves further miniaturization has been developed, and a line width of 20 nm or 10 nm has been used for a leading-edge process. The degree of difficulty in processing has increased along with an increase in the degree of miniaturization, and various techniques are currently under development using various approaches in terms of the materials, devices, and processing methods.

In view of the above situation, the applicant of the present application developed a plasma etching gas that includes a saturated fluorohydrocarbon represented by the formula (1): $C_xH_yF_z$ (wherein x is 3, 4, or 5, and y and z are independently a positive integer, provided that y>z) that can deal with a leading-edge dry etching process, and reported that a saturated fluorohydrocarbon having a small number of fluorine atoms exhibits a performance better than that of monofluoromethane that is used to etch a silicon nitride film (see Patent Literature 1).

For example, the following methods are known as a method for producing 2-fluorobutane (i.e., saturated fluorohydrocarbon represented by the formula (1)).

Patent Literature 2 discloses that 2-fluorobutane was obtained in a yield of 46% by bringing N,N-diethyl-3-oxomethyltrifluoropropylamine (fluorinating agent) into contact with 2-butanol.

Patent Literature 3 discloses that sec-butyl fluoride was produced by bringing sulfur hexafluoride into contact with a sec-butyllithium cyclohexane/hexane solution.

Patent Literature 4 discloses a method that brings 2-butanol into contact with a fluorine-containing ylide in the presence of 2-butene.

Patent Literature 5 discloses that 2-fluorobutane was obtained by hydrogenating 2-fluorobutadiene in the presence of a catalyst.

Non-Patent Literature 1 discloses a method that subjects an olefin compound to bromohydrination wherein methylenecyclobutane is reacted with aqueous N-bromosuccinimide in the absence of a solvent to obtain 1-(bromomethyl)cyclobutanol.

These pieces of literature disclose a method for producing 2-fluorobutane. However, these pieces of literature disclose only a little information about the purity of the resulting 2-fluorobutane as well as impurities, and do not disclose a method for efficiently purifying 2-fluorobutane.

CITATION LIST

Patent Literature

Patent Literature 1: WO2009/123038
Patent Literature 2: JP-A-59-46251
Patent Literature 3: JP-A-2009-292749
Patent Literature 4: JP-A-2013-095669
Patent Literature 5: U.S. Pat. No. 2,550,953

Non-Patent Literature

Non-Patent Literature 1: Journal of Organic Chemistry, Vol. 19, 2915 (1971)

SUMMARY OF INVENTION

Technical Problem

The inventor of the invention reported that high-purity 2-fluorobutane could be obtained by subjecting crude 2-fluorobutane obtained by a reaction to distillation, drying, and denitrification-deoxidation (Japanese Patent Application No. 2013-045131).

However, the resulting 2-fluorobutane had high purity, but included butene as impurities.

It is desirable to more efficiently remove butene from the viewpoint of industrial productivity. Since butene (separated from 2-fluorobutane) is gaseous at room temperature, the handling of butene is subjected to various industrial restrictions. In view of the above situation, the inventor conducted extensive studies in order to easily remove most of the butene from crude 2-fluorobutane.

JP-T-2002-524431 discloses a method for removing unsaturated impurities from a fluorinated butane wherein a fluorotrichloroethylene product included in 1,1,1,3,3-pentafluorobutane is removed through the addition of a diatomic molecule (e.g., hydrogen chloride, fluorine, chlorine, or hydrogen).

The inventor applied the method disclosed in JP-T-2002-524431 to purification of crude 2-fluorobutane, and used a highly reactive reactant (e.g., fluorine or chlorine). As a result, decomposition (dehydrofluorination) of 2-fluorobutane (that easily undergoes dehydrofluorination) occurred.

A method that hydrogenates butene using hydrogen that exhibits low reactivity with 2-fluorobutane may also be used. According to this method, however, since butane (gaseous substance) is produced as impurities, it is impossible to achieve the object of easily removing impurities.

An object of the invention is to provide a conversion method that converts butene into compounds having a boiling point higher than that of 2-fluorobutane, and can easily remove impurities (e.g., butene) from crude 2-fluorobutane to obtain high-purity 2-fluorobutane, and a method for purifying 2-fluorobutane that utilizes the conversion method.

Solution to Problem

The inventor conducted further studies in order to solve the above problem. As a result, the inventor found that butene can be converted into compounds having a high boiling point while suppressing decomposition of 2-fluorobutane by bringing 2-fluorobutane that includes butene into contact with a brominating agent that can form a bromonium ion and water or an alcohol having up to 4 carbon atoms in an aprotic polar solvent. This finding has led to the completion of the invention.

Several aspects of the invention provide the following conversion method (see (1) to (3)) and method for purifying 2-fluorobutane (see (4) and (5)).

(1) A conversion method including bringing crude 2-fluorobutane that includes 5 to 50 wt % of butene into contact with a brominating agent that can form a bromonium ion in an aprotic polar solvent in the presence of water or an alcohol having up to 4 carbon atoms to convert the butene into compounds having a boiling point higher than that of 2-fluorobutane.

(2) The conversion method according to (1), wherein the brominating agent is N-bromosuccinimide.

(3) The conversion method according to (1) or (2), wherein the aprotic polar solvent has a boiling point higher than that of 2-fluorobutane by 30° C. or more.

(4) A method for purifying 2-fluorobutane including converting the butene into compounds having a boiling point higher than that of 2-fluorobutane using the conversion method according to any one of (1) to (3), collecting 2-fluorobutane from the reaction mixture, and purifying the collected 2-fluorobutane by distillation.

(5) The method for purifying 2-fluorobutane according to (4), wherein the collecting of 2-fluorobutane from the reaction mixture includes collecting 2-fluorobutane under a reduced pressure of 10 to 70 kPa.

Advantageous Effects of Invention

The aspects of the invention thus provide a conversion method that converts butene into compounds having a boiling point higher than that of 2-fluorobutane, and can easily remove impurities (e.g., butene) from crude 2-fluorobutane to obtain high-purity 2-fluorobutane, and a method for purifying 2-fluorobutane that utilizes the conversion method.

DESCRIPTION OF EMBODIMENTS

Exemplary embodiments of the invention are described in detail below.

A conversion method according to one embodiment of the invention includes bringing crude 2-fluorobutane that includes 5 to 50 wt % of butene into contact with a brominating agent that can form a bromonium ion in an aprotic polar solvent in the presence of water or an alcohol having up to 4 carbon atoms to convert the butene into compounds having a boiling point higher than that of 2-fluorobutane.

The crude 2-fluorobutane used in connection with one embodiment of the invention may be produced using the method described in Journal of Organic Chemistry, Vol. 44, 3872 (1979), or the method described in Bulletin of the Chemical Society of Japan, Vol. 52, 3377 (1979). The method described in Journal of Organic Chemistry, Vol. 44, 3872 (1979) produces 2-fluorobutane by fluorinating 2-butanol (raw material) using a poly(hydrogen fluoride) pyridine complex as a fluorinating agent, and the method described in Bulletin of the Chemical Society of Japan, Vol. 52, 3377 (1979) produces 2-fluorobutane by fluorinating 2-butanol (raw material) using N,N-diethylaminohexafluoropropane (prepared from hexafluoropropene and diethylamine) as a fluorinating agent. Note that the crude 2-fluorobutane may also be produced using a method that treats 2-bromobutane or a 2-(alkylsulfonyloxy)butane with an alkali metal fluoride (e.g., potassium fluoride or cesium fluoride).

The crude 2-fluorobutane produced using the above method includes butene (mainly 1-butene (boiling point: −6.3° C.), (E)-2-butene (boiling point: 0.9° C.), and (Z)-2-butene (boiling point: 3.7° C.)) in addition to 2-fluorobutane (boiling point: 24 to 25° C.).

Examples of the brominating agent that can form a bromonium ion include an inorganic bromine compound such as sodium hypobromite and bromine; an amide/imide-based brominating agent such as N-bromoacetamide, N-bromosuccinimide, N-bromophthalimide, N-bromosaccharin, 1,3-dibromo-5,5-dimethylhydantoin, dibromoisocyanuric acid, and monosodium bromoisocyanurate; and a cyclic bromoketone-based brominating agent such as 2,4,4,6-tetrabromo-2,5-cyclohexadienone and 5,5-dibromomeldrum's acid. Among these, an amide/imide-based brominating agent such as N-bromoacetamide, N-bromosuccinimide, N-bromophthalimide, N-bromosaccharin, 1,3-dibromo-5,5-dimethylhydantoin, dibromoisocyanuric acid, and monosodium bromoisocyanurate is preferable, and N-bromosuccinimide and 1,3-dibromo-5,5-dimethylhydantoin are more preferable.

The brominating agent that can form a bromonium ion is preferably added in an amount (on a bromine atom basis) of 0.9 to 3 equivalents, and more preferably 1.1 to 2 equivalents, based on the total amount of butene. If the brominating agent is added in too small an amount, the conversion ratio may decrease, and the amount of residual butene may increase. If the brominating agent is added in too large an amount, the brominating agent may not be sufficiently dissolved in a water-soluble solvent that is used in connection with one embodiment of the invention, and a troublesome post-treatment may be required. Moreover, since the brominating agent is a corrosive substance, a reactor and the like may be damaged.

The water or the alcohol having up to 4 carbon atoms used in connection with one embodiment of the invention functions as a nucleophile for butene. Note that the water or the alcohol having up to 4 carbon atoms used in connection with one embodiment of the invention may be hereinafter referred to as "nucleophile". Examples of the alcohol having up to 4 carbon atoms include a saturated lower alcohol such as methanol, ethanol, n-propanol, isopropanol, n-butanol, sec-butanol, and isobutanol; and an unsaturated lower alcohol such as allyl alcohol and propargyl alcohol.

It is preferable to use water or methanol, and it is more preferable to use water from the viewpoint of ease of handling.

The nucleophile is preferably added in an amount of 1 to 5 equivalents, more preferably 2 to 3 equivalents, based on the total amount of butene. If the nucleophile is added in too small an amount, the conversion ratio of butene may decrease. If the nucleophile is added in too large an amount, the solubility of the brominating agent may decrease, the reaction system may become complex, and a troublesome post-treatment may be required.

The aprotic polar solvent used in connection with one embodiment of the invention preferably has a boiling point higher than that of 2-fluorobutane by 30° C. or more.

Specific examples of the aprotic polar solvent include a ketone-based solvent such as acetone and 2-butanone; an ether-based solvent such as tetrahydrofuran, tetrahydropyran, ethylene glycol dimethyl ether, and diethylene glycol dimethyl ether; a nitrile-based solvent such as acetonitrile and propionitrile; an amide-based solvent such as N,N-dimethylformamide, N,N-dimethylacetamide, 1,3-dimethyl-2-imidazolidinone, and N-methylpyrrolidone; a sulfur-containing solvent such as dimethyl sulfoxide and sulfolane; and the like. Among these, dimethylacetamide and dimethyl sulfoxide are preferable due to a high capability to dissolve an amide product and an imide product produced by the reaction.

The aprotic polar solvent is preferably used in a 1 to 5-fold amount (on a volume basis), and more preferably a 1.5 to 3-fold amount, based on the amount of the crude 2-fluorobutane (raw material). If the aprotic polar solvent is used in too small an amount, the reaction may proceed rapidly depending on the type of the brominating agent. If the aprotic polar solvent is used in too large an amount, a complex waste treatment may be required.

The reaction temperature when converting the butene into compounds having a boiling point higher than that of 2-fluorobutane is preferably −30° C. to +25° C., and more preferably −10° C. to 0° C. If the reaction temperature is too low, solidification (coagulation) may occur depending on the combination of the water-soluble solvent and the water or the combination of the water-soluble solvent and the alcohol used for the reaction. If the reaction temperature is too high, 2-fluorobutane may easily volatilize (i.e., the amount of loss may increase).

The reaction time is determined taking account of the way in which the brominating agent that can form a bromonium ion is added, but is normally 0.5 to 10 hours, and preferably 1 to 5 hours. If the reaction time is too short, the reaction may not be completed, and the amount of residual butene may increase. If the reaction time is too long, side reactions (e.g., bromination of 2-fluorobutane) may easily occur.

The reaction may be effected in an arbitrary way. It is preferable to use a method that charges a reactor with the aprotic polar solvent and the nucleophile, cools the reactor to an arbitrary temperature, charges the reactor with the crude 2-fluorobutane that includes the butene, and adds the brominating agent in several parts while stirring the mixture. If the brominating agent is added all together, the reaction may proceed rapidly, and bumping may occur due to generation of heat.

For example, the progress of the reaction may be monitored by gas chromatography, and the brominating agent may be added when a large amount of butene remains.

2-Fluorobutane is collected from the reaction system using a normal method such as a method that collects 2-fluorobutane directly from the reaction mixture under reduced pressure; or a method that subjects the reaction mixture or a solution prepared by diluting the reaction mixture with water to an extraction process using an organic solvent (e.g., hydrocarbon or halogenated hydrocarbon), followed by washing with a reducing agent (e.g., sodium thiosulfate aqueous solution, sodium sulfite aqueous solution, or sodium hydrogen sulfite aqueous solution).

It is preferable to collect 2-fluorobutane directly from the reaction mixture under reduced pressure since it is unnecessary to provide equipment that reduces the amount of loss of 2-fluorobutane having a low boiling point due to volatilization, and sufficiently cool the chemicals such as the solvent.

When collecting 2-fluorobutane under reduced pressure, a collection receiver and a trap are provided to the reactor, and cooled using a refrigerant (e.g., dry ice-ethanol). The pressure inside the system is normally decreased gradually from 70 kPa to about 40 kPa to collect 2-fluorobutane. When using a solvent having a high boiling point (150° C. or more) (e.g., amide-based solvent or sulfoxide-based solvent), it is preferable to decrease the pressure inside the system to about 10 kPa to increase the collection ratio of 2-fluorobutane since the solvent is not easily volatilized.

It is preferable to heat the reactor to 30 to 50° C. in order to prevent a decrease in temperature due to latent heat of vaporization. When the boiling point of the aprotic polar solvent is relatively low, the solvent may also be collected in the collection receiver and the trap, and separated by the subsequent rectification.

The collected 2-fluorobutane may be purified by rectification in order to remove a trace amount of butene and other impurities included therein to further increase the purity. The solvent is also separated by rectification when 2-fluorobutane is collected together with the solvent. The rectification pressure (gauge pressure) is normally set to a value between normal pressure and 10 atmospheres, and preferably set to a value between normal pressure and about 5 atmospheres.

The ratio of the reflux rate to the distillate rate (hereinafter may be referred to as "reflux ratio") is preferably set to 30:1 or more in order to efficiently separate a trace amount of butene that easily gasifies. If the reflux ratio is too low, it may be difficult to efficiently separate the butene, and sufficiently increase the purity of 2-fluorobutane. Moreover, the amount of the first fraction may increase, and the amount of 2-fluorobutane (that is collected as a product) may decrease. If the reflux ratio is too high, collection (per distillation) may take time, and the rectification time may increase to a large extent. A batchwise rectification method may be used when the production volume is small. When the production volume is large, a continuous rectification method that utilizes several rectifying columns may be used. An extractive distillation operation that utilizes an extraction solvent may be performed in combination with rectification.

A solvent that undergoes two-phase separation with the reaction mixture or a solution obtained by diluting the reaction mixture with water is preferable as an organic solvent that is used as the extraction solvent. According to this method, it is possible to separate the target product into the organic solvent layer, and separate compounds (bromohydrin product) having a high boiling point into the layer of the reaction mixture or a solution obtained by diluting the reaction mixture with water. Specific examples of the organic solvent include a hydrocarbon such as n-pentane, n-hexane, n-heptane, n-octane, cyclopentane, cyclohexane, cycloheptane, cyclooctane, benzene, toluene, and xylene; a halogenated hydrocarbon such as dichloromethane, chloroform, carbon tetrachloride, 1,2-dichloroethane, chlorobenzene, and dichlorobenzene; and the like.

EXAMPLES

The invention is further described below by way of examples. Note that the scope of the invention is not limited to the following examples. The unit "%" refers to "wt %" unless otherwise indicated.

The following analysis conditions were used in connection with the examples.
Gas chromatography analysis (GC analysis)
Device: HP-6890 manufactured by Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated at 20° C./min, and held at 40° C. for 10 minutes
Injection temperature: 200° C.
Carrier gas: nitrogen
Split ratio: 100/1
Detector: FID
Analysis of impurities (gas chromatography-mass spectrometry)
GC device: HP-6890 manufactured by Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated at 20° C./min, and held at 240° C. for 10 minutes
MS device: 5973 NETWORK manufactured by Agilent Technologies
Detector: EI (accelerating voltage: 70 eV)

Production Example 1

A 1 L glass reactor equipped with a stirrer, a dropping funnel, and a trap was charged with 86 g of spray-dried potassium fluoride (manufactured by Aldrich), 2-(p-toluenesulfonyloxy)butane, and 400 mL of diethylene glycol. Nitrogen was introduced into the reactor through the outlet tube of the trap to subject the mixture to a nitrogen atmosphere. The reactor was immersed in an oil bath, and heated to 90° C. 135 g of 2-(p-toluenesulfonyloxy)butane was added dropwise to the mixture from the dropping funnel over 2.5 hours. The mixture was reacted at 90° C. for 5 hours, and a volatile component produced by the reaction was collected in the trap immersed in a dry ice-ethanol bath. After lowering the temperature of the oil bath to 80° C., two glass traps immersed in a dry ice-ethanol bath were connected to the reactor in series. A pressure controller and a vacuum pump were connected to the outlet of the glass traps. The vacuum pump was operated, and the pressure inside the system was lowered stepwise to 50 to 45 kPa, 35 to 30 kPa, and 30 to 25 kPa using the pressure controller to collect a volatile component in the glass traps. The contents of the trap and the two glass traps were combined, and analyzed by gas chromatography. It was found that the mixture (22 g) included 1-butene (5.23% by area), (E)-2-butene (19.91% by area), (Z)-2-butene (13.04% by area), 2-fluorobutane (58.30% by area), and other impurities (3.52% by area).

Example 1

A 300 mL glass reactor equipped with a stirrer and a Dimroth condenser was charged with 60 mL of dimethyl sulfoxide and 15 g of water, and the mixture was cooled to 0° C., and stirred. A refrigerant (0° C.) was circulated through the Dimroth condenser. The reactor was charged with 40 g of the crude 2-fluorobutane obtained in Production Example 1, and the mixture was stirred for 10 minutes. 36 g of N-bromosuccinimide was added to the reactor in three equal parts (12 g) at intervals of 20 minutes. After stirring the mixture for 1 hour, the mixture was analyzed by gas chromatography. As a result, 1-butene (0.03% by area), (Z)-2-butene (0.01% by area), 2-fluorobutane (30.39% by area), and other impurities (1.11% by area) were detected, and production of a bromohydrin product was observed in the high retention time region. A compound produced by bromination of 2-fluorobutane was not observed.

Example 2

The Dimroth condenser was removed from the reactor used in Example 1, and a receiver and a glass trap were sequentially attached to the reactor. A pressure controller and a vacuum pump were connected to the outlet of the glass trap. The vacuum pump was operated, and the pressure inside the system was lowered stepwise to 70 to 60 kPa, 40 to 30 kPa, and 30 to 25 kPa using the pressure controller to collect a volatile component in the receiver and the glass trap. The contents of the receiver and the glass trap were combined, and analyzed by gas chromatography. It was found that 2-fluorobutane was collected in a ratio of 98.70% by area, and the collection ratio (on a weight basis) was 92% based on the crude 2-fluorobutane used in Example 1.

Example 3

A still (distillation still) was charged with 138 g of 2-fluorobutane obtained by repeating the operations of Examples 1 and 2, and distillation was performed using a KS rectifying column (manufactured by Toka Seiki Co., Ltd., column length: 60 cm, packing material: Heli Pack No. 1). A refrigerant (−10° C.) was circulated through a condenser, and total reflux was effected for about 1 hour. The still was heated from 45° C. to 65° C. while observing the temperature of the top part of the column and the amount of the 2-fluorobutane remaining in the still. A fraction was then distilled at a reflux ratio of 30:1. 99.9% by area or more of a 2-fluorobutane fraction was obtained when about 1.5 hours had elapsed after the start of distillation. 91 g of 2-fluorobutane (99.95% by area) was thus obtained. The fraction was analyzed to find that the fraction included 1-butene (53 ppm by area), (Z)-2-butene (85 ppm by area), and isobutyl fluoride (362 ppm by area) as impurities.

Example 4

A 200 mL glass reactor equipped with a stirrer and a Dimroth condenser was charged with 30 mL of diethylene glycol dimethyl ether and 7.6 g of water, and the mixture was cooled to 0° C., and stirred. A refrigerant (0° C.) was circulated through the Dimroth condenser. The reactor was charged with 20 g of the crude 2-fluorobutane obtained in Production Example 1, and the mixture was stirred for 10 minutes. 18 g of N-bromosuccinimide was added to the reactor in three equal parts (6 g) at intervals of 20 minutes. After stirring the mixture for 1 hour, the mixture was analyzed by gas chromatography. As a result, 1-butene (0.26% by area), (Z)-2-butene (0.10% by area), 2-fluorobutane (29.48% by area), and other impurities (2.64% by area) were detected, and production of a bromohydrin product was observed in the high retention time region. A compound produced by bromination of 2-fluorobutane was not observed.

Example 5

The Dimroth condenser was removed from the reactor used in Example 4, and a receiver and a glass trap were sequentially attached to the reactor. A pressure controller and a vacuum pump were connected to the outlet of the glass trap. The vacuum pump was operated, and the pressure inside the system was lowered stepwise to 70 to 60 kPa and 50 to 40 kPa using the pressure controller to collect a volatile component in the receiver and the glass trap. The contents of the receiver and the glass trap were combined, and analyzed by gas chromatography. It was found that 2-fluorobutane was collected in a ratio of 96.78% by area, and the collection ratio (on a weight basis) was 82% based on the crude 2-fluorobutane used in Example 4.

Example 6

A reaction was effected in the same manner as in Example 1, except that the solvent was changed from dimethyl sulfoxide to 60 mL of N,N-dimethylacetamide.
The resulting mixture was analyzed by gas chromatography. As a result, 1-butene (0.4% by area), (Z)-2-butene (0.06% by area), 2-fluorobutane (29.71% by area), and other impurities (2.17% by area) were detected, and production of a bromohydrin product was observed in the high retention region. A compound produced by bromination of 2-fluorobutane was not observed.
The Dimroth condenser was removed from the reactor, and a receiver and a glass trap were sequentially attached to the reactor. A pressure controller and a vacuum pump were connected to the outlet of the glass trap. The vacuum pump was operated, and the pressure inside the system was lowered stepwise to 70 to 60 kPa, 40 to 30 kPa, and 30 to 25 kPa using the pressure controller to collect a volatile component in the receiver and the glass trap. The contents of the receiver and the glass trap were combined, and analyzed by gas chromatography. It was found that 2-fluorobutane was collected in a ratio of 94.13% by area, and the collection ratio (on a weight basis) was 89% based on the crude 2-fluorobutane.

Example 7

A reaction was effected in the same manner as in Example 1, except that 38.9 g of 1,3-dibromo-5,5-dimethylhydantoin was used instead of 36 g of N-bromosuccinimide, and the reaction temperature was changed to −20° C.

The resulting mixture was analyzed by gas chromatography. As a result, 1-butene (0.01% by area), (Z)-2-butene (0.002% by area), (E)-2-butene (0.005% by area), 2-fluorobutane (38.33% by area), and other impurities (2.60% by area) were detected, and production of a bromohydrin product was observed in the high retention time region. A compound produced by bromination of 2-fluorobutane was not observed.

Example 8

A reaction was effected in the same manner as in Example 1, except that 27 g of methanol was used instead of 15 g of water, and the reaction temperature was changed to −10° C.

The resulting mixture was analyzed by gas chromatography. As a result, 1-butene (1.45% by area), (E)-2-butene (1.23% by area), (Z)-2-butene (2.85% by area), 2-fluorobutane (20.98% by area), and other impurities (4.21% by area) were detected. Production of a bromomethoxybutane product was observed in the high retention time region, and a compound produced by bromination of 2-fluorobutane was not observed.

Example 9

A 300 mL glass reactor equipped with a stirrer and a Dimroth condenser was charged with 60 mL of dimethyl sulfoxide and 15 g of water, and the mixture was cooled to 0° C., and stirred. A refrigerant (0° C.) was circulated through the Dimroth condenser. The reactor was charged with 40 g of the crude 2-fluorobutane obtained in Production Example 1, and the mixture was stirred for 10 minutes. 36 g of N-bromosuccinimide was added to the reactor in three equal parts (12 g) at intervals of 20 minutes. After stirring the mixture for 1 hour, the mixture was analyzed by gas chromatography. As a result, 1-butene (0.02% by area), (Z)-2-butene (0.02% by area), 2-fluorobutane (30.58% by area), and other impurities (1.02% by area) were detected, and production of a bromohydrin product was observed in the high retention time region. A compound produced by bromination of 2-fluorobutane was not observed.

After cooling the reaction mixture to 0° C., 10 mL of n-hexane was added to the reaction mixture. The resulting mixture was stirred for a little over 5 minutes to extract 2-fluorobutane including unreacted butene, and the n-hexane layer was separated. The extraction operation was then repeated twice, and the n-hexane layer was collected, sequentially washed with a 5% sodium hydrogen sulfite aqueous solution and a saturated sodium chloride solution, and dried over anhydrous magnesium sulfate. After filtering off the magnesium sulfate, the filtrate (n-hexane layer) was analyzed by gas chromatography. It was found that almost the entirety of 1-butene, (Z)-2-butene, and 2-fluorobutane was extracted with n-hexane, and the bromohydrin product was not extracted with n-hexane (i.e., remained in dimethyl sulfoxide (solvent)). It was thus confirmed that 2-fluorobutane could be easily separated from the bromohydrin product.

Comparative Example 1

A reaction was repeatedly effected in the same manner as in Production Example 1 to obtain 249 g of a mixture including 1-butene (5.43% by area), (E)-2-butene (20.02% by area), (Z)-2-butene (13.17% by area), 2-fluorobutane (57.89% by area), and other impurities (3.49% by area). The mixture was subjected to distillation using the distillation column used in Example 3. A refrigerant (−10° C.) was circulated through the condenser, and total reflux was effected for about 1 hour. The still was heated from 40° C. to 50° C. while observing the temperature of the top part of the column and the amount of the crude 2-fluorobutane remaining in the still. A fraction was then distilled at a reflux ratio of 45:1 to 30:1. Butene was thus evaporated. 11 hours were required until the purity of the fraction reached 99.0% by area. 86 g of 2-fluorobutane (99.12% by area) was thus obtained.

It was thus found that it takes time to remove butene by subjecting crude 2-fluorobutane including a large amount of butene to distillation, and it is difficult to apply such a process on an industrial scale from the viewpoint of production efficiency.

Comparative Example 2

A 100 mL glass reactor equipped with a gas introduction tube and a stirring bar was charged with 30 mL of 1,1,2-trifluorotrichloroethane. The reactor was immersed in a dry ice-ethanol bath, and cooled to −70° C. The reactor was charged with 20 g of the crude 2-fluorobutane produced in Production Example 1, and 10.7 g of chlorine gas was introduced into the reactor from the gas introduction tube through a mass flow controller over about 1 hour. After stirring the mixture at −70° C. for 30 minutes, the mixture was analyzed by gas chromatography. As a result, 1-butene (2.21% by area), (E)-2-butene (3.41% by area), (Z)-2-butene (3.09% by area), and a compound produced by chlorination of 2-fluorobutane (13.4% by area) were detected.

The invention claimed is:

1. A conversion method comprising bringing crude 2-fluorobutane that includes 5 to 50 wt % of butene into contact with a brominating agent that can form a bromonium ion in an aprotic polar solvent in the presence of water or an alcohol having up to 4 carbon atoms to convert the butene into bromine containing compounds having a boiling point higher than that of 2-fluorobutane.

2. The conversion method according to claim 1, wherein the brominating agent is N-bromosuccinimide.

3. The conversion method according to claim 1, wherein the aprotic polar solvent has a boiling point higher than that of 2-fluorobutane by 30° C. or more.

4. A method for purifying 2-fluorobutane comprising converting the butene into compounds having a boiling point higher than that of 2-fluorobutane using the conversion method according to claim 1, collecting 2-fluorobutane from a reaction mixture, and purifying the collected 2-fluorobutane by distillation.

5. The method for purifying 2-fluorobutane according to claim 4, wherein the collecting of 2-fluorobutane from the reaction mixture includes collecting 2-fluorobutane under a reduced pressure of 10 to 70 kPa.

* * * * *